(12) United States Patent
Nitto

(10) Patent No.: US 6,387,061 B1
(45) Date of Patent: May 14, 2002

(54) POSTURE AND WEIGHT DISTRIBUTION ANALYZER

(76) Inventor: Dennis J. Nitto, 10 W. End Ct., West End, NJ (US) 07740

( * ) Notice: Subject to any disclaimer, the term of this patent is extended or adjusted under 35 U.S.C. 154(b) by 0 days.

(21) Appl. No.: 09/739,996

(22) Filed: Dec. 19, 2000

(51) Int. Cl.⁷ .............................................. A61B 5/103
(52) U.S. Cl. ..................................................... 600/587
(58) Field of Search ................................ 600/587, 594, 600/595

(56) References Cited

U.S. PATENT DOCUMENTS 4,832,049 A * 5/1989 Matsushita et al. ......... 600/594
5,979,067 A * 11/1999 Waters ......................... 33/512
6,231,527 B1 * 5/2001 Sol ............................. 600/595

* cited by examiner

*Primary Examiner*—Samuel G. Gilbert
*Assistant Examiner*—Pamela Wingood
(74) *Attorney, Agent, or Firm*—Robert M. Skolnik

(57) ABSTRACT

A diagnostic apparatus employs a spaced grid and a centerline on a vertically mounted mirror to reflect the skeletal position of a patient. The patient stands on two scales which measure the weight borne by each of the patient's legs. The output of each scale is displayed on the mirror. An aperture is formed in the mirror to enable the patient to be photographed. The photograph may be printed on paper bearing the grid pattern and the centerline.

7 Claims, 2 Drawing Sheets

POSTURE AND WEIGHT DISTRIBUTION ANALYZER

BACKGROUND OF THE INVENTION

1. Field of the Invention

The present invention relates to a posture and weight distribution analyzer for medical treatment.

2. Description of the Related Art

Various posture and/or weight distribution devices are shown in the prior art.

Gregory, et al, U.S. Pat. No. 4,033,329, shows a machine for checking skeletal structure incorporating measurements of the legs on platforms 17 and 18 and of the pelvis with arms 46 and 47.

Gregory, U.S. Pat. No. 4,036,213 discloses the method involved with the machine of the other Gregory, et al. patent.

Rotella, U.S. Pat. No. 4,425,713 covers a mechanical postureometer.

Pile, U.S. Pat. No. 4,492,236 discloses a machine with measures and corrects the overall attitude of a patient relative to a horizontal reference plane.

Kokayakawa, et al., U.S. Pat. No. 4,600,012 disclose an impinging laser light on a patient to measure the position reflected light relative to the position of the impinged light.

Curtis, U.S. Pat. No. 4,823,476 shows a grid pattern based on relative human body proportions first advanced by Leonardo DaVinci.

Matsushita, et al., U.S. Pat. No. 4,832,049, relates to another laser light measuring system of the type shown in Kokayakawa, et al.

Arme, U.S. Pat. No. 5,080,109, shows a system somewhat similar to your invention using a video camera, a computer display and a light pen to generate a database in the computer of locations on the body determined by the light pen.

Benesh, et al, U.S. Pat. No. 5,088,504 relates to a machine similar to that shown in the Gregory patents; however, weight measurements from scales 22 and 24, are displayed on display 30.

Greenawalt, U.S. Pat. No. 5,443,974 shows cord grids for a patient's side and back.

Grassi, U.S. Pat. No. 5,823,974 establishes an initial patient position, then lets the patient assume a normal patient position and records the results on a pantograph display.

The spinal analysis machine offered by S.A.M., 660 Middlegate Road, Henderson, Nev. 89015 has a cord grid in the manner of Greenawalt, U.S. Pat. No. 5,443,974

SUMMARY OF THE INVENTION

This invention relates to the field of diagnostic apparatus in general, and in particular, diagnostic apparatus, in the fields of medicine, chiropractic medicine, and allied health professions. The apparatus employs a grid system, dual scales, and photographic and computer apparatus to record and evaluate a patient's postural misalignments.

In general health care practice, many conditions and ailments may be traced to a postural condition, which places undue stress on vital nerves and tissues. As a consequence, the detection of these postural misalignments is imperative before any method of correction may be prescribed.

This invention relates to apparatus for use in the proper alignment of skeletal features of a human patient.

Health care practitioners, especially chiropractic physicians, are interested in ascertaining the skeletal position of a patient, particularly that of the entire skeletal frame, so that, for example, proper treatment of the spine, the application of orthotic devices for the feet or heel lifts may be prescribed in order to correct mal-positioned bone bond structure. This treatment facilitates proper alignment of the skeletal frame.

An important aspect of skeletal position is the patient's weight distribution (i.e. when a patient is standing, what weight is on each foot).

The present invention enables the medical professional to easily ascertain the relative position of selected skeletal features in lateral directions. In association with this position information, weight distribution information on each of a patient's legs is also provided. The skeletal position is determined by reflecting the patient's posture from a mirrored grid. The mirrored grid has apertures formed therein to display the weight readings of two scales on which the patient is standing. The image of the patient is photographed and may be connected to a printer on which the patient's posture is imprinted on graph paper having the same pattern as the grid on the mirror.

In this manner, the medical professional may adjust the overall attitude of the patient in relation to a referenced vertical grid plane so as to move the patient's skeletal features into a position to properly align the head and upper body of the patient, relative to a preferred grid pattern to more perfectly align the entire skeletal frame.

The apparatus of the invention may be used by physicians and surgeons concerned with spinal abnormalities such as orthopedic surgeons, neurologists, psychiatrists and general medical practitioners for spinal screening procedures; physical therapists for use as a monitoring device curing coursed of physical therapy and rehabilitation; chiropractic physicians for monitoring spinal subluxations displacement and postural distortion thereof; school districts for scoliosis screening examinations; and gymnasiums and general fitness centers for monitoring muscle balance, spinal positioning and training programs.

A principal object of this invention to provide therapeutic apparatus for properly aligning, with a predetermined reference(s), selected skeletal features of a patient under treatment.

Another object of this invention is to provide apparatus, as aforesaid, allowing for said alignment to correct lateral displacements of said skeletal features from corresponding predetermined references.

Still another object of this invention is to provide apparatus as aforesaid, which enables a physician to select treatment alternatives to adjust the position of the patient under treatment, relative to a referenced plane, in a manner to correct any displacement of the skeletal features of the patient from said predetermined reference.

It is another object of this invention to provide apparatus, as aforesaid, which has measuring devices for measuring the patient's weight distribution.

A more particular object of this invention is to provide the vertical axis alignment device, as aforesaid, which ascertains the proper attitude of the spinal column of the patient relative to a predetermined reference grid.

A still further object of this invention is to provide a vertical axis alignment device, as aforesaid, having display means incorporated therein, which indicates the preferred and actual attitudes of the selected vertical axis of the patient.

Other objects and advantages of this invention will become apparent from the following description taken in connection with the accompanying drawings, wherein is set forth by way of illustration and example, an embodiment of this invention.

The foregoing, as well as further objects and advantages of the invention will become apparent to those skilled in the art from a review of the following detailed description of my invention, reference being made to the accompanying drawings.

DETAILED DESCRIPTION OF THE PREFERRED EMBODIMENT

Figure 1:
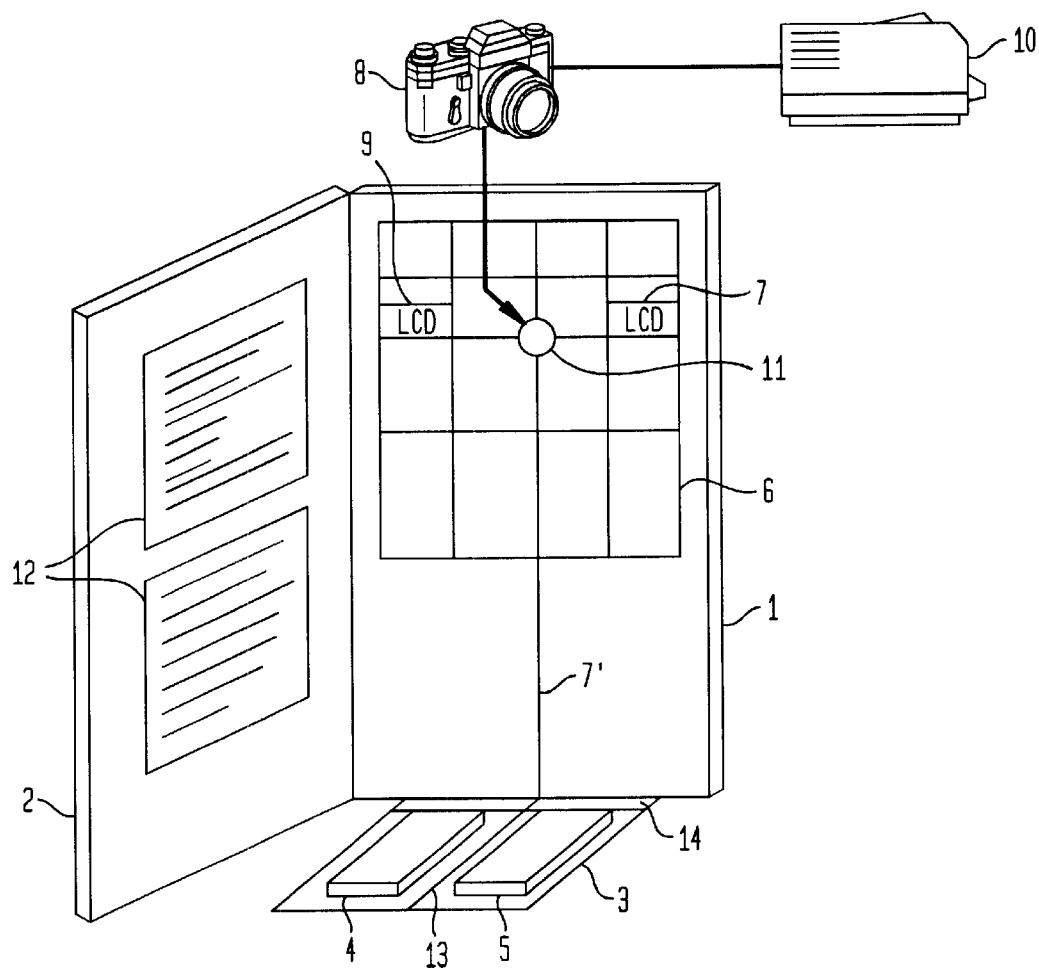
FIG. 1 is a perspective view of my invention.
Figure 2:
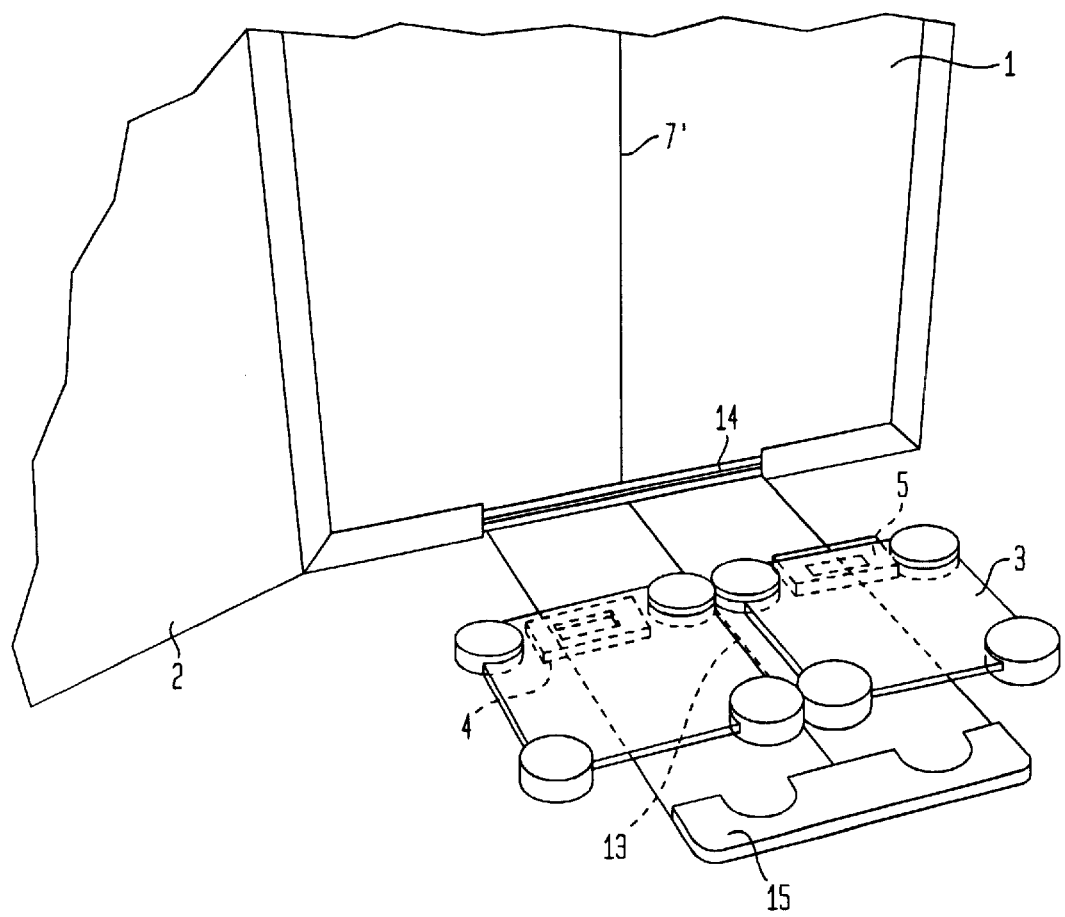
FIG. 2 is a perspective view of a portion of FIG. 1.

Like reference numerals have been used to designate like parts of the invention in FIGS. 1–2. As shown in FIG. 1 the apparatus includes a mirror 6 mounted on a vertical panel 1. A grid consisting of five horizontal lines and four vertical lines about centerline 7 is formed on mirror 6. The spacing of the grid lines on mirror 6 should be within the following ranges to accurately depict the skeletal alignment.

The mirror 6 has a central aperture 11 formed therein to enable a patient to be photographed therethrough with a camera 8. The camera 8 may be connected to a printer so that a photographic representation of the patient can be printed onto grid-patterned paper having a grid pattern imprinted thereon which matches the grid pattern on mirror 6.

Two displays 7 and 9 are mounted in mirror 6. The displays are connected to respective left and right scales 5 and 4.

Two additional panels 2 and 3 are attached to the vertical panel 1. Panel 2 is hinged to panel 1 for providing support so that both panels may be freestanding. Panel 2 may also be used to mount educational information in the form of charts. A footplate 3 is hinged to the bottom of vertical panel 1. Footplate 3 has two scales 4 and 5 mounted thereon. The scales are mounted on either side of centerline 13. The centerline 13 is a continuation of the centerline 7'. Centerlines 7 and 13 are center of gravity lines for the patient.

If a wall mount is desired, panel 2 may be disconnected from vertical panel 1. Panel 1 is then mounted directly to a wall.

FIG. 2 is a perspective view of the footplate and load scale portions of FIG. 1. As shown in FIG. 2, hinge-mounting 14 is attached in proximity to the bottom of vertical panel 1. Footplate 3 with scales 4 and 5 mounted thereon is attached to hinge 14. A heel support 15 may be provided for the patient while standing on footplate 3.

Further modifications to the apparatus of the invention may be made without departing from the spirit and scope of the invention.

I claim:

1. A diagnostic apparatus for determining a patient's postural deficiencies comprising:

a first panel for supporting a patient in a standing position;

scale means on said first panel for measuring the patient's weight on each of the patient's legs;

a second panel mounted vertically with respect to said first panel; mirror means mounted on said second panel for reflecting a patient's image while said patient is standing on said first panel;

a plurality of grid lines formed in spaced apart relation on said mirror means;

a center line formed on said mirror means and on said first panel;

display means connected to said second panel and to said scale means for displaying the patient's weight on each of the patient legs as measured by said scale means; and aperture means formed in said mirror means for enabling a patient to be photographed through said mirror means.

2. The apparatus of claim 1, further including a third panel connected to said second panel for supporting said second panel.

3. The apparatus of claim 2 further including photographic means cooperating with said aperture means for photographing a patient.

4. The apparatus of claim 3 further including printer means connected to said photographic means for printing a photograph of a patient.

5. The apparatus of claim 4 wherein said photograph of a patient is printed on a representation of said plurality of grid lines and said center line.

6. A diagnostic apparatus for determining a patient's postural deficiencies comprising:

a generally rectangular platform member having a platform surface;

scale means attached to said platform surface; for providing readings a first panel formed adjacent to and above said platform surface;

hinge means connected to said first panel and said platform surface for hingedly mounting said platform surface to said first panel;

a mirror mounted on said first panel;

grid lines formed on said mirror;

a centerline formed on said mirror and on said platform surface;

display means mounted on said mirror means and connected to said scale means for displaying the readings of said scale means; and an aperture formed in said mirror to enable a photograph to be taken therethrough.

7. The diagnostic apparatus of claim 6 further including heel support means attached to said platform surface for supporting a patient standing on said platform surface.

* * * * *